United States Patent [19]

Laudenslager et al.

[11] Patent Number: 5,383,199
[45] Date of Patent: Jan. 17, 1995

[54] APPARATUS AND METHOD FOR OPTICALLY CONTROLLING THE OUTPUT ENERGY OF A PULSED LASER SOURCE

[75] Inventors: James B. Laudenslager, Long Beach; Fred G. Kinley, Mission Viejo, both of Calif.

[73] Assignee: Advanced Interventional Systems, Inc., Irvine, Calif.

[21] Appl. No.: 909,054

[22] Filed: Jul. 2, 1992

[51] Int. Cl.⁶ ................................................ H01S 3/10
[52] U.S. Cl. ............................................ 372/25; 372/31
[58] Field of Search ............................. 372/25, 27, 31

[56] References Cited

U.S. PATENT DOCUMENTS

| | | | |
|---|---|---|---|
| 4,611,270 | 9/1986 | Klauminzer et al. | 364/183 |
| 4,641,912 | 2/1987 | Goldenberg | 350/96.10 |
| 4,732,448 | 3/1988 | Goldenberg | 350/96.18 |
| 4,962,502 | 10/1990 | Adams | 372/31 |
| 4,998,794 | 3/1991 | Holzman | 350/96.18 |
| 5,016,964 | 5/1991 | Donnelly | 350/96.18 |
| 5,128,601 | 7/1992 | Orbach et al. | 372/25 |
| 5,151,909 | 9/1992 | Davenport et al. | 372/25 |

OTHER PUBLICATIONS

Bennett and Byer, "Variable Laser Attenuators—Old and New" Laser Focus, Apr. 1983 pp. 55-63.

*Primary Examiner*—Rodney B. Bovernick
*Assistant Examiner*—Robert E. Wise
*Attorney, Agent, or Firm*—Flehr, Hohbach, Test, Albritton & Herbert

[57] ABSTRACT

Apparatus for optically controlling the output energy of a pulsed laser source comprising a laser producing a plurality of laser pulses in a laser beam. An optical attenuator is disposed in the laser beam to attenuate the energy in the laser beam to provide an attenuated laser beam, and a pick-off is provided for sensing the energy in the attenuated laser beam. A controller is coupled to the pick-off for controlling the optical attenuator to vary the energy in the attenuated laser beam to thereby vary the output fluence from the apparatus.

25 Claims, 4 Drawing Sheets

APPARATUS AND METHOD FOR OPTICALLY CONTROLLING THE OUTPUT ENERGY OF A PULSED LASER SOURCE

This invention relates to an apparatus and method for optically controlling the output energy of a pulsed laser source and more particularly to such an apparatus and method for use in pulsed ultraviolet excimer laser angioplasty.

In the past, changing the pulse energy output from a laser has been accomplished for discharge pumped excimer lasers and optically pumped infrared lasers by lowering or raising the voltage of the primary excitation means for the laser. However in the preferred embodiment for excimer lasers, a magnetic saturable switch(s) are used in the electric discharge circuit. It has been found that the use of magnetic saturable switches limits the operating range of the high voltage excitation and changes of 20% and greater to control the laser output pulse changes the timing between the various circuits coupled by magnetic switches and has caused the laser discharge to become unstable. In addition, it has been found that changing the output energy by changing the high voltage excitation can cause premature electrode wear. It also can decrease gas and window lifetime. Also in gas excimer lasers, as the discharge cycles are accumulated on a gas mix, the gas mix degrades causing degradation of the output energy from the laser. In Klauminzer et al. U.S. Pat. No. 4,611,270 there is a disclosed a method and means of controlling the output of a pulsed laser. The high voltage electric discharge means is adjusted to control the output. Thus, as the gas mix degrades lowering the energy output from the laser, the high voltage to the high voltage discharge means is increased. The energy deposited from the electric discharge means is given by $E = \frac{1}{2}CV^2$, or as the voltage squared. Therefore, as the gas mix degrades, more electrical energy is introduced into the laser and although this raises the laser energy output, all of the excess electrical energy ends up in gas degradation and discharge arcs which sputter electrodes, increasing erosion and causing window contamination. In addition, it has been found that changing the pulse energy by changing the high voltage discharge voltage is a non-linear relationship, making calibration more difficult to program energy changes during lasing of the laser. There is therefore a need for a new and improved apparatus and method for changing the output energy of a pulsed laser.

In the prior art for optical attenuation as taught by Byer et al, in an article entitled "Variable Attenuators—Old and New" in Laser Focus for April 1983, pages 55-62 attenuation concepts disclosed therein do not work reliable for high pulsed energy and or power densities from large aperture laser beams. Greater than 100 kW/cm² peak power fluences and energy fluences greater than 50 mJ/cm² for pulsed ultraviolet sources with beam cross sectional areas greater than 1.25/cm² cannot be achieved with the known methods without severe degradation due to optical damage or the limitation of physical size of the attenuator. Also the attenuator should not optically degrade or distort the spatial beam profile or substantially deviate the beam angular propagation direction. The use of screen attenuators with a coupling arrangement that images the screen pattern onto an angioplasty catheter is generally not acceptable because the energy fluence is not constant over each individual fiber optic.

In general, it is an object of the present invention to provide an apparatus and method for optically controlling the output energy of a pulsed laser source.

Another object of the invention is to provide an apparatus and method of the above character in which an optical attenuator is utilized.

Another object of the invention is to provide an apparatus and method of the above character in which the optical attenuator is a polarizer.

Another object of the invention is to provide an apparatus and method of the above character in which the optical attenuator does not significantly deviate or spatially distort the propagation of the laser beam.

Another object of the invention is to provide an apparatus and method of the above character for use with an ultraviolet high pulse energy large cross section (greater than 10 MJ/pulse, greater than $1 \times 1/cm^2$) laser beam.

Another object of the invention is to provide an apparatus and method of the above character in which the optical attenuator can be programmed for a range of energy.

Another object of the invention is to provide an apparatus and method of the above character is to provide an apparatus and method which can be utilized with an excimer laser to produce a predetermined ablation fluence from a fiberoptic angioplasty catheter.

Another object of the invention is to provide an apparatus and method of the above character in which a coupler is provided which has a fixed spot size to handle the largest sized catheter.

Another object of the invention is to provide an apparatus and method of the above character in which the catheter is positioned at or near the waist of the beam.

Another object of the invention is to provide an apparatus and method of the above character in which the beam size is set and the energy adjustment is made with a single control on the laser output.

Additional objects and features of the invention will appear from the following description in which the preferred embodiments are set forth in detail in conjunction with the accompanying drawings.

In general, the apparatus for optically controlling the output energy of a pulsed laser source is comprised of a laser producing a plurality of laser pulses in a laser beam. An optical attenuator is disposed in the laser beam to provide a laser beam with attenuated laser output energy. Pick-off means is provided for sensing the energy in the attenuated laser output beam. Control means is coupled to the pick-off means for controlling the optical attenuator to vary the laser output energy.

Figure 1:
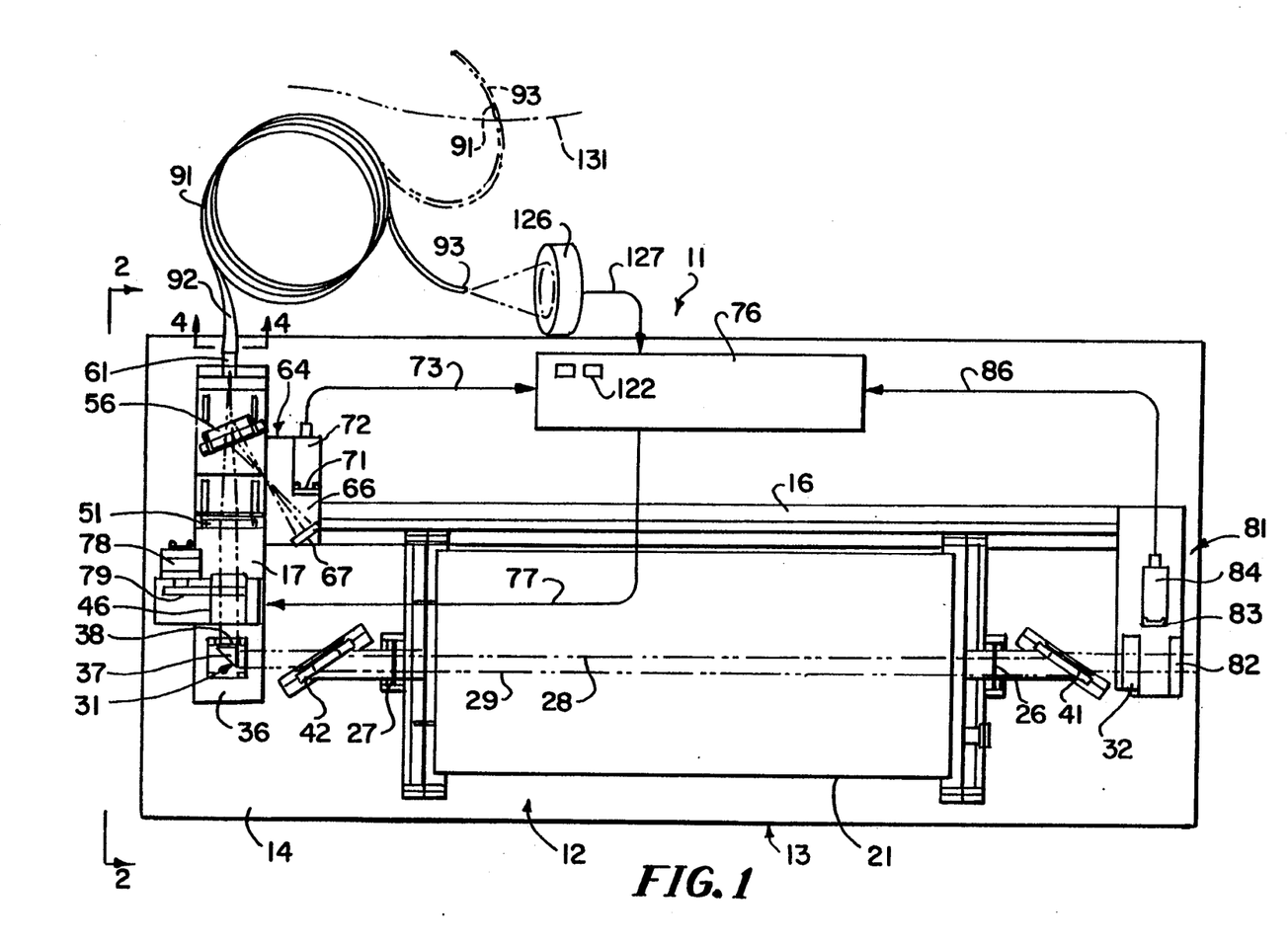
FIG. 1 is a top plan view of a laser apparatus incorporating the present invention.

More specifically, as shown in the drawings, the laser apparatus 11 for optically controlling the output energy of a pulsed laser source consists of a laser resonator or laser source 12 which is supported by a mounting or support structure 13. The mounting structure 13 is made from materials which have a high stiffness-to-weight ratio, as for example aluminum extrusions. The mounting structure includes a support platform 14. A primary rail 16 is mounted on the support platform 14. A coupler rail 17 is mounted on the primary rail 16 (see FIG. 2).

The laser apparatus 11 also includes various optical elements hereinafter described which are hard-mounted on the mounting structure 13 and on the rails as can be seen in the drawings, to prevent accidental misalignment of the optical components. The rails are mechanically isolated from a laser vessel or laser head 21 of the laser 12 in order to avoid misalignment due to laser vessel mechanical expansion and contraction, and also to avoid long-term misalignment which can be caused by operation of the laser.

Let it be assumed that the laser 12 is conventional, as for example a 308 nm xenon chloride (XeCl) excimer pulsed laser which is utilized in laser angioplasty. The laser 12 can be a conventional commercially available laser such as supplied by Advanced Interventional Systems, Inc. The laser vessel 21 is provided with windows 26 and 27 at opposite ends thereof with the laser beam 28 travelling through the vessel 21 along a path 29. As shown in FIG. 1, the excimer laser resonator 12 includes a plano partial reflective output coupler mirror 31 and a spherical concave highly reflective mirror 32 which are disposed on opposite ends of the laser vessel 21. The mirrors 31 and 32 form a stable hemispherical resonator from which a spatial mode structure can be determined. This spatial mode structure can be used to determine the spatial width of the propagated laser beam 28. By way of example, one embodiment of an excimer laser of this type had the rear mirror 32 having a radius of curvature of 10 meters and a spacing between the mirrors 31 and 32 of 1.0 meter around a 2×2 cm$^2$ aperture excimer discharge. Assuming a Gaussian beam core and a building up of the resonator modes as Hermite-Gaussian, 325 spatial modes are calculated to exist. The beam propagation can therefore be defined as being the square root of 325 times diffraction limited (TDL), with a beam waist at the resonator output coupler mirror 31. The rear mirror 32, because of its slight concavity, acts to fold the laser beam back onto itself across the discharge in the optical cavity formed by the laser vessel 21 and serves to even out nonuniformities in the beam caused by the gas discharge. The output coupler mirror 31 serves as a coupler lens and is utilized to focus the laser beam and produces a laser beam having the desired waist of a proper diameter for a purpose hereinafter described. The mirror 31 is shown as a right-angle transmissive fused silica prism which is provided with a surface 36 which is coated with a laser output coupler coating to serve as the laser resonator mirror output coupler. For example, it can be provided with a coating which is from 50–80% reflective at 308 nm at 0° so that 50–20% of the light that passes through the surface 36 reflects off of the hypotenuse 37 which can be uncoated by total internal reflection in the prism.

This eliminates the need for a difficult 45°-p polarized coating when the laser output energy is linearly polarized in the p direction with respect to the 90° turn. The remaining surface 38 of the prism 31 can be anti-reflection coated at 308 nm at 0°. Thus it can be seen that the prism 31 serves as an output coupler mirror as well as a 90° turning mirror.

First and second Brewster fused silica windows 41 and 42 are provided for coupling laser light into and out of the laser gas vessel 21. As is well known to those skilled in the art, such windows are disposed at an angle which will transmit the laser light in a particular polarization state without any substantial loss of energy. Such windows are disposed at Brewster's angle to prevent Fresnel reflections.

Thus it can be seen that the right-angle prism 31 makes it possible to fold the optical axis of the laser apparatus of the present invention at right angles to shorten the overall length of the optical train. The use of the 45° prism ensures that the laser beam will be propagated at a fixed angle through the prism.

The laser beam 28 after it has been passed through a 90° turning angle by the prism 31, passes through an optical attenuator 46 of the type described in co-pending application Ser. No. 07/907,893 filed Jul. 2, 1992, (A-55645). As disclosed therein, such an optical attenuator is an optically contacted, thin film polarizer. The attenuator 46 can have a $T_p$ that is greater than 95%; and a $T_s$ which is less than 5% and in which the incoming and outgoing surfaces are anti-reflection coated for 308 nm at 0°. Such an optical attenuator 46 is suitable for attenuating the energy of the laser beam because the output from the laser 12 is inherently polarized due to the use of the Brewster windows 41 and 42. As described in said co-pending application, the attenuator 46 can be utilized for high-intensity pulsed ultraviolet light emitted by excimer lasers and provides long-term stable operation without high throughput loss or damage.

The laser beam after passing through the optical attenuator 46 passes through a fused silica coupler lens 51. The coupler lens 51 can be in the form of a simple plano-convex lens of a suitable focal length, as for example approximately 17 cm and having anti-reflection coatings formed on surfaces thereof for 308 nm at 0°. The coupler lens 51 is used to form the target catheter input focal beam waist. Since the X-Y position of this optic 51 with respect to the laser beam determines the focal spot location, it is positioned at the proper X-Y location in the beam to align the focal spot with respect to the catheter coupler location as hereinafter described. This permits the coupler lens 51 to be hard-mounted without the requirement of a tilt.

The laser beam, after passing through the coupler lens 51, passes through a wedge 56 which by way of example can be a 3° wedge which permits most of the energy in the laser beam to pass through the wedge 56 with a small percentage being reflected off of each of the surfaces of the wedge for monitoring purposes. The wedge 56 is a fused silica plano optic with a slight wedge (30) between the front and back surfaces and is located in the laser beam at a slight angle. By way of example, if the wedge 56 is uncoated, approximately 4% of the total energy can be reflected back from each of the surfaces. If an anti-reflection coating is provided on one or both of the surfaces of the wedge 56, the energy reflected back can be made to less than 1% of the total energy. In any event, a small fraction of the energy passing through the optic in the form of the wedge 56 is reflected from the front and back surfaces due to Fresnel reflections. By way of example, wedge 56 can have the first surface anti-reflection coated for 308 nm at 20°, whereas the second surface can be left uncoated.

The light passing through the wedge 56 is supplied to a coupler 61 which is of a type adapted to be connected to a catheter utilized in laser angioplasty as hereinafter described. Since the wedge 56 serves as the pick-off optic and is located after the coupling lens 51, the laser light which is picked off has the same focal characteristics as the laser beam propagating into the catheter bundle, making it easy to filter out stray light from the signal with the use of apertures.

The optical energy which is picked off by the wedge 56 is supplied into an output energy (fluence) monitor 64 which includes a housing 66 supported on the coupler rail 17. The picked off laser light beam passes through apertures (not shown) in the housing 66 to filter out stray light and is directed onto a Lambertian scattering element 67 mounted within the housing 66. The element 67 can be formed of any suitable material, as for example Teflon. Alternatively, a polycrystalline alumina may be utilized. The element 67 serves to scatter the pick-off beam at a very large solid angle. A portion of this scattered beam is detected by suitable means such as photodiode 71 which can be adjustably positioned within the housing 66 with respect to its spacing from the element 67. Thus, the photodiode 71 serves to convert optical information supplied by the element 67 into an electrical signal which is immediately preamplified in a preamplifier 72 provided within the housing 66. The immediate preamplification and the shielding provided by the housing 66 serves to minimize the effect of any electrical noise created by the pulse power from the laser 12.

The output from the photodiode 71 and the preamplifier 72 is supplied by a cable 73 to a controller 76 which is utilized for driving a stepper motor 78 for causing rotation by a timing belt drive 79 of the optical attenuator 46 in a manner hereinafter described. The controller 76 includes a microprocessor (not shown) which uses a computer-generated algorithm for driving the stepper motor 78 in accordance with the information supplied from the photodiode 71.

Thus, it can be seen that the pick-off Fresnel reflections from the wedge 56 can be utilized to monitor laser energy input into the catheter output coupler 61. Since the focal beam area can be calculated to a high degree of accuracy and since the pick-off beam has the same beam focal characteristics as the actual beam, actual laser output energy (fluence) present at the catheter input can be inferred from the pick-off energy. Also, it should be appreciated that beam plane stability can be monitored by the use of a quad cell photodiode or CCD array. By knowing the laser fluence present at the catheter input from the energy pick-off, suitable feedback control to control the rotation angle of the polarizer can be made in order to reach a target operating fluence, such as if it is desired to change operating fluence during an angioplasty procedure as hereinafter described.

In the laser apparatus 11, a total energy monitor 81 is also used and it includes a Lambertian scatter element 82 of a suitable material such as Lexan which is utilized for scattering the very small amount of laser light which passes through the high reflector mirror 32. This scattered light is measured by a photodiode 83 to supply an electrical signal which is amplified in a preamplifier 84 and the information supplied to the controller 76 through a cable 86. Thus the photodiode 83 makes it possible to measure the raw laser output energy and to track it over time to ascertain whether or not there is laser gas degradation. The information supplied by the photodiode 83 also can be utilized in connection with the knowledge of the transmission of the attenuator 46 as a function of angle to rotate the attenuator to the desired angle to transmit the desired amount of laser energy.

The coupler 61 of the laser apparatus 11 is adapted to be coupled to the input of a catheter 91 of a conventional type such as supplied by Advanced Interventional Systems, Inc. of Irvine, Calif. 92718, which has a multiple fiber optic bundle extending from the input to the output. It is provided with an input or proximal end 92 and a distal or output end 93.

Figures 2, 3, 4:
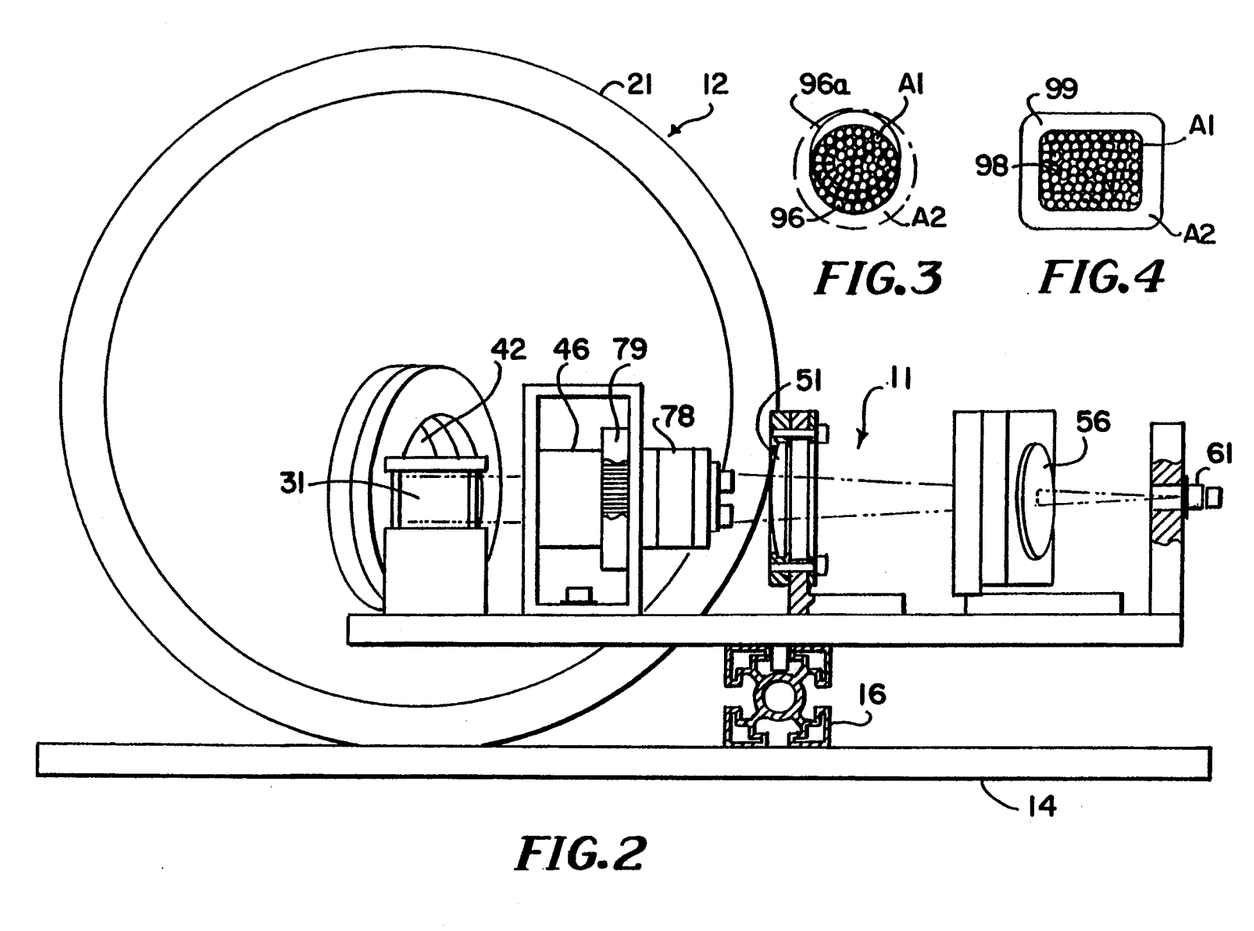
FIG. 2 is a side elevational view taken along the line 2—2 of FIG. 1.
FIG. 3 is a cross-sectional view showing the manner in which the input of a catheter having a circular multiple fiber optic bundle is overfilled with a circular laser spot.
FIG. 4 is a cross sectional view taken along the line 4—4 of FIG. 1 showing the manner in which a rectangular input bundle of a catheter is utilized with the rectangular spot from an excimer laser.

In FIGS. 3 and 4, there are cross-sectional views showing circular and rectangular input bundles of fiber optic elements. To couple the input of the catheter 91 into the output coupler 61 of the laser apparatus 11, it should be appreciated that for any simple optical system more than several times diffraction limited, the locations most immune to optical misalignment are the local beam waists of the laser beam along the axis of propagation of the laser beam since these areas are not affected by radial displacements of the beam. Thus the beam waist or a region in close vicinity thereto is the most desirable location for the catheter input spot in order to minimize the effect of mechanical misalignment of the optical assembly of the laser apparatus on the ability to couple catheters effectively thereto.

From the calculated spatial mode structure of the laser resonator 12, it is possible to calculate within a very good approximation the resulting beam waist for any lens combination in the coupler optical train. For an excimer angioplasty catheter, such as the catheter 91, the catheter input is comprised of a bundle of close-packed individual fiber optics to maximize the active fiber core area within the smallest bundle diameter. For any laser coupler for such catheters, a finite amount of beam overfill is required to ensure that all of the fibers receive laser illumination within manufacturing tolerances of the input bundle position, as shown in FIG. 2. Excess beam overfill requires more laser energy. Since a circle is the result of the minimization of the perimeter for a given area, it is the preferred coupler bundle shape to minimize laser overfill area and hence the required laser energy. Thus, a circular fiber optic bundle 96 is shown in FIG. 3 which has an input area of $A_1$. The laser spot 97 shows the required beam spot overfill required to ensure that all fibers receive laser illumination and also to accommodate misalignment of the input of the catheter with respect to the laser spot. Area $A_2$ is the area required for the beam spot overfill to accommodate such misalignment. The excess beam overfill equals $1-(A_1/A_2)$.

For realistic excimer lasers, the natural beam shape is rectangular, for which a minimum perimeter to area is obtained as a square. Since losses are incurred in forcing a rectangular excimer beam to become circular, the realistic optimum catheter bundle geometry is square. Thus, in FIG. 4 there is shown a square fiber optic bundle 98 and a square beam spot 99. The same equation which is utilized for a circular input bundle as shown in FIG. 3 can be utilized for the square input bundle shown in FIG. 4 to determine the minimum spot size.

Figure 5:
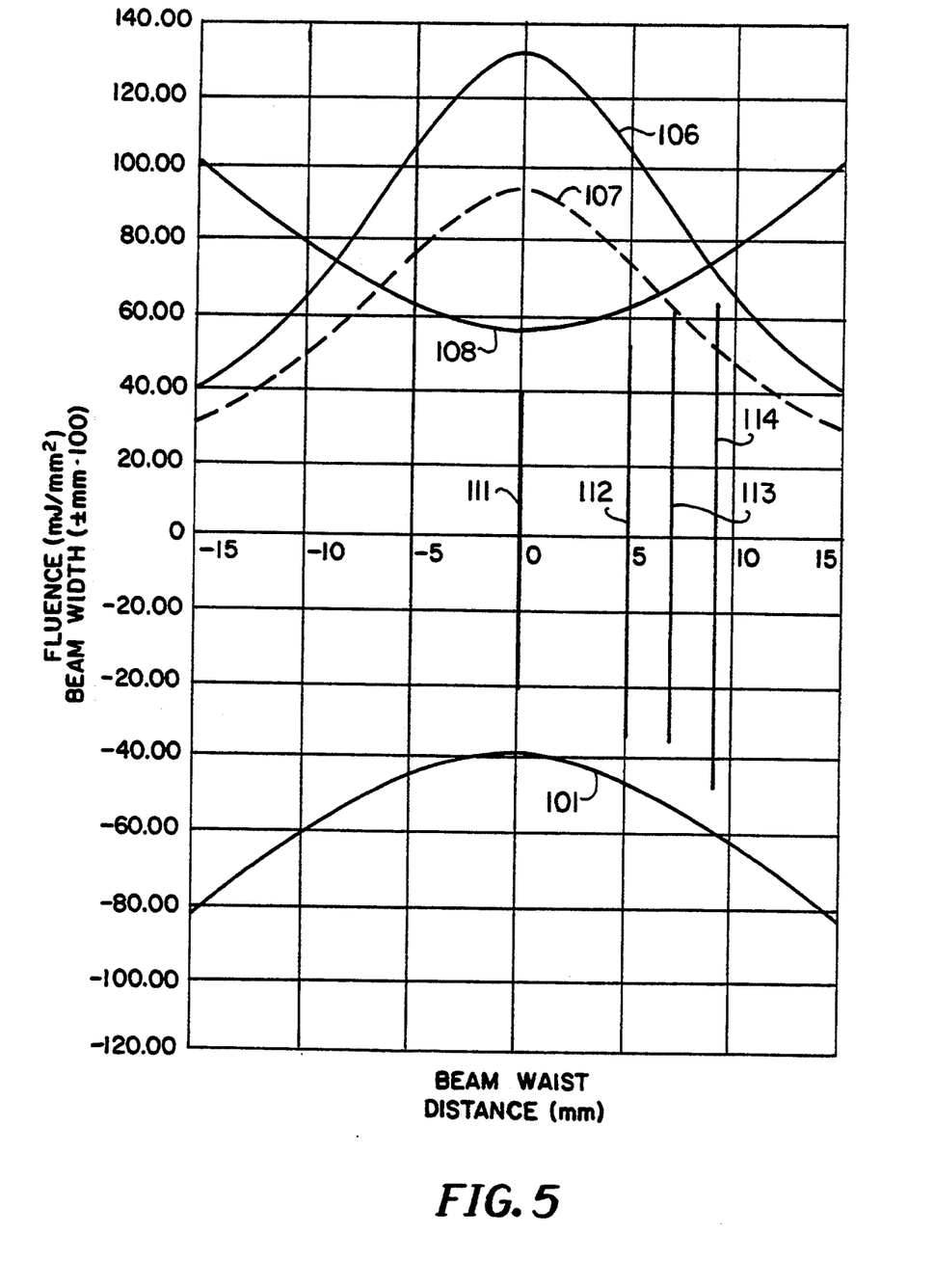
FIG. 5 is a graph showing the positions of the inputs of a family of catheters of various sizes in the waist of the laser beam.

In FIG. 5, the graph shows the calculated focal beam waist diameter and resulting minimum laser fluence along the Z axis of propagation for the laser resonator 12 utilized in the laser apparatus 11 in which a 17 cm plano-convex coupler lens 51 is utilized. As shown in FIG. 5, such a coupler lens does not focus the beam down to a point, but such a lens does focus the beam down and causes it to flatten out to form a beam waist 101 which is the minimum spacing between the two hyperbolic lines 102 and 103 shown in FIG. 5. The top solid line 106 represents the input fluence in Joules/mm$^2$ being supplied to the input to the catheter 91. Thus, for an output energy of 170 milliJoules/mm$^2$, the line 106 shows that at the waist 101 a fluence of approximately 130 mJ/mm$^2$ is supplied to the input of the catheter. Since the total laser output energy is controlled by the optical attenuator 46, this output energy can be increased or decreased without changing the location of the beam waist or any of its geometrical properties to thereby vary the input fluence into the catheter 91.

The output fluence from the catheter 91 is represented by the dashed line 107 shown in FIG. 5 which shows that approximately 80% of the energy which is introduced into the catheter input is supplied as a typical output fluence for the catheter. By actually measuring the output energy or fluence from the catheter 91 and dividing it by the catheter's active area, the catheter can be calibrated so that for a certain output fluence a given input fluence is required. This makes it possible to utilize the internal energy monitor 64 with its photodiode 71 and its associated electronics including the preamplifier 72 to control the output fluence at the distal extremity of the catheter 91. Thus, as long as optical distortion does not occur in the laser beam, it is possible to vary the output fluence at the distal extremity of the catheter by controlling the input fluence to the input of the catheter.

In FIG. 5 there is also shown a family of catheters 111, 112, 113 and 114 having various input dimensions and the manner in which they would be positioned with respect to the laser beam waist 101 at the coupler 61. The most used and highest fluence catheters are placed at the beam waist with the larger, lower fluence catheters being displaced very slightly axially away from the beam waist until their input bundles are completely filled by the laser spot. As shown in FIG. 5, there is a gap between the bundle diameter of the catheters and the laser beam. This gap represents the overfill. Thus it can be seen that there has been provided a means for coupling a family of catheters into a fixed focal geometry with varying catheter input bundle sizes. By way of example, let it be assumed that the laser apparatus 11 of the present invention provides a laser beam which has a focal beam waist of 1.15 mm in diameter and a focal spot area of 1.33 mm$^2$. Thus, by way of example, the catheters 111, 112, 113 and 114 can have diameters of 1.3 mm, 1.6 mm, 2.0 mm and 2.2 mm, respectively. The fiber optic bundles generally have a dimension which is substantially less than this outer dimension and all have an input area which is substantially less than the 1.33 mm$^2$ of the focal spot so that there is overfill as represented by the lengths of the catheters 111, 112, 113 and 114 in FIG. 5 and the gap between the ends of the same and the hyperbolic lines 102 and 103. The inputs of all the catheters are positioned so that they are within the Rayleigh range of the beam waist area, which is an area determined along the Z axis where the beam area increases by a factor of 2.

Figure 6A:
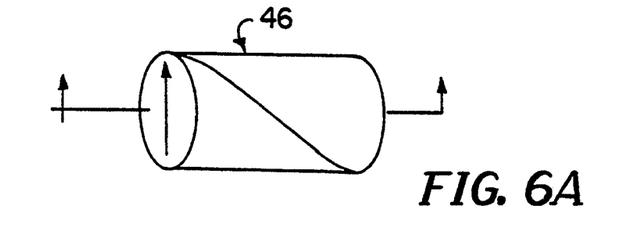
FIGS. 6A, 6B and 6C are isometric views showing various positions of the polarizer utilized as an optical attenuator in the laser apparatus in FIG. 1.
Figure 6B:
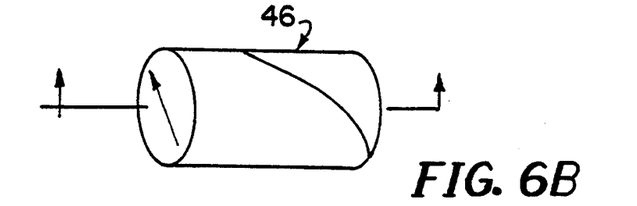
Figure 6C:
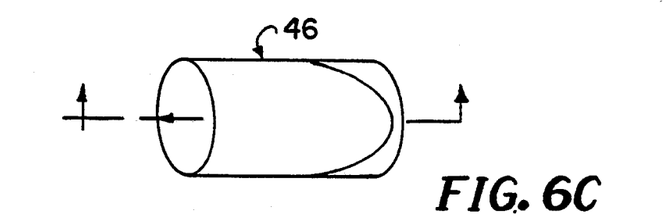

In connection with ascertaining the output fluence from the distal extremity of the catheter 91, let it be assumed that the optical attenuator or polarizer 46 is mounted so that its preferred axis of transmission, i.e. the axis of the cylinder 46 shown in FIGS. 6A, 6B and 6C is aligned at an angle of rotation with respect to the direction of polarization of the laser beam. A partial transmission of the polarized laser fluence is obtained which varies as the cosine of $\theta$, where $\theta$ is the angle between the polarizer preferred axis and the laser beam polarization state. Various rotational positions of the optically contacted, thin film polarizer 46 are shown in FIGS. 6A, 6B and 6C. In FIG. 6A the angle $\theta$ is 0°. Thus at $\theta=0°$, the following equation where E represents fluence can be written:

$$E_{OUT}=E_{IN}\cos^2(0°)=E_{IN}.$$

Thus it can be seen that the transmission of the polarizer is substantially unity.

By rotating the polarizer 46 through 45°, the same equation can be solved:

$$E_{OUT}=E_{IN}\cos^2(45°)=(0.5)E_{IN}.$$

Thus, by rotation of the polarizer 46 through 45°, the output fluence has been decreased by one-half.

By rotation of the polarizer 46 through another 45° to provide a total angle of 90°, the same equation again can be solved:

$$E_{OUT}=E_{IN}\cos^2(90°)=0.$$

Figure 7:
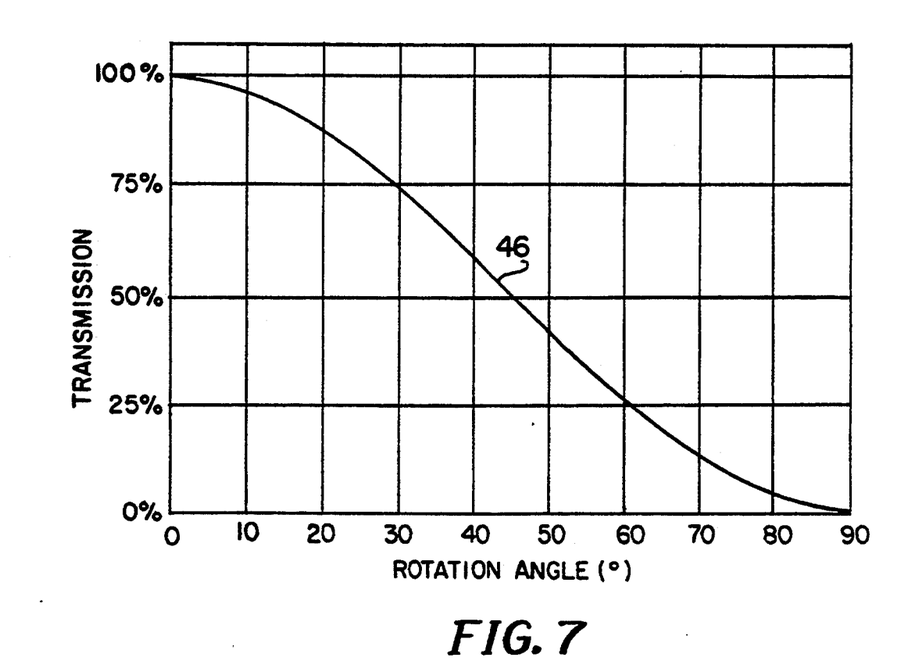
FIG. 7 is a graph showing laser output versus polarizer angle using the polarizer shown in FIG. 6.

Thus it can be seen that by rotation of the polarizer 46 between 0° and 90°, 100% to 0% transmission of the polarized laser fluence is obtained. This laser output or fluence versus polarizer angle is shown in FIG. 7, in which the transmission through the attenuator for the rotation angle is shown by the curve 116. The curve 116 represents the amounts of p and s components of polarization of the laser beam, with the curve 116 reflecting the following equation:

$$p(\cos(a)^2)+s(\sin(a)^2).$$

From this transmission as a function of rotation angle curve 116, the required polarization rotation for a desired laser throughput can be directly determined.

Operation and use of the laser apparatus 11 in performing an laser angioplasty procedure may now be briefly described as follows. Let it be assumed that the catheter 91 has its input or proximal end 92 connected to the output coupler 61 in a suitable manner such as a conventional threaded ferrule (not shown). By way of example, let it be assumed that the laser apparatus 11 produces approximately 200 mJ per pulse in a 2×2 cm$^2$ beam cross-sectional area. Also let it be assumed that the catheter 91 for use in a plaque ablation procedure requires an energy density or output fluence from the distal or output end 93 of the catheter of about 50 mJ/mm$^2$. It is necessary to calibrate the catheter 91 to provide this output fluence. To do this, let it be assumed that the catheter 91 has a cross-sectional area of $A_1$ which means an energy of 50 mJ/mm$^2$ times $A_1$ is necessary to be set as the desired reading from a conventional energy meter 121 measuring the output fluence from the distal extremity 93 of the catheter 91 and supplying it through a cable 122 to the controller 76. This area $A_1$ may be supplied to the controller 76 by sensing the size of the catheter 91 or may be directly entered by use of a keypad (not shown).

The optical attenuator or polarizer 46 can be rotated through 90° as shown in FIG. 6C so that it is a default mode of maximum attenuation or minimum throughput. The distal extremity 93 of the catheter 91 outside the patient is placed in the energy detector 121 as shown in FIG. 1 and the attenuator angle is varied to permit more laser energy to be supplied to the input or proximal end 92 of the catheter 91. More laser input energy into the input of the catheter results in more laser energy output at the distal extremity. The attenuator or polarizer 46 is then adjusted until the controller 76 reads the correct setting from the energy meter 121, which in this case is energy equals 50 mJ/mm$^2$ times area $A_1$. The internal energy monitor 64 through its photodiode 71 reads the total laser energy input to the catheter 91 and the energy meter 126 reads the total energy output from the catheter 91. The difference represents the catheter coupling and transmission losses which by way of example can be 20%. Thus it can be seen that the catheter 91 is calibrated by ascertaining the output fluence versus the input fluence or energy as a function of attenuator rotational position. This calibrates the catheter 91 for the optic alignment and laser output of the laser apparatus 11. A set point is then introduced into the controller 76 by a single control 122 which can be in the form of a set of conventional up-down switches. The controller 76 monitors this set point and automatically adjusts the throughput of the polarizer 46 to maintain that set input fluence to what is now a calibrated catheter 91. This laser energy input into the input of the catheter 91 is directly proportional to a given output fluence at the distal extremity 93 of the catheter 91.

The calibrated catheter 91 can then be introduced into the patient 131 as represented by the dotted lines in FIG. 1 in a conventional manner so that its distal extremity is in the vicinity of the plaque to be ablated. The operator then inserts through the single control 122 of the controller 76 the desired output fluence at the distal extremity of the catheter 91 to cause the attenuator 46 to rotate to the proper angular position. If it is desired to change the output fluence, this can be changed while the catheter 91 is in the patient. It is only necessary to change the attenuator throughput by a proportional amount by adjustment of the single control 122 to obtain an equal percentage change of the output fluence at the distal extremity 92 of the catheter 91 since the coupling and transmission losses are nearly linear for the catheter 91.

Thus it can be seen that after the catheter 91 has been calibrated by the use of the energy output meter 126 in the manner hereinbefore described, the catheter 91 can be introduced into the patient in a conventional manner to position the distal extremity of the catheter at a location where it is desired to perform an ablation procedure. With the polarizer 46 positioned in the proper angular position to deliver the desired amount of laser energy to the input of the catheter, the desired amount of output fluence appears at the distal extremity of the catheter to perform the desired ablation. If it is determined during the procedure that more or less output fluence is desired, this can be readily obtained by adjusting the single control 122 on the controller 76 to achieve the desired output fluence to complete the ablation procedure. After the ablation procedure has been completed, the catheter 91 can be withdrawn from the patient in a conventional manner.

In accordance with the present invention, the coupler 61 has a fixed spot size so that it is capable of handling the largest size catheter of the family of catheters to be utilized with the apparatus. Thus, the beam size is set and the energy adjustment is made with a single control on the laser output. The attenuator or polarizer does not change the beam direction, spatial profile or pulse width appreciably and provides substantially linear attenuation. If it is not linear, the attenuator should have a known calibrated attenuation function so that the hereinbefore described calibration procedures between the input and output fluence can be readily ascertained.

From the foregoing it can be seen that there has been provided and apparatus and method for optically controlling the output energy of a pulsed laser in which the laser itself is not controlled, as for example by controlling the voltage applied for the electric discharge. Rather the output energy at the distal extremity of the catheter is controlled by precision rotation of an optical polarizer 46 which serves to attenuate the laser beam without affecting the operation of the laser 22. Such changes in output energy can be readily achieved with rapidity and with great precision. The polarizer 46 does not deviate the laser beam or degrade the spatial uniformity of the propagating laser beam or drastically change its divergence nor is this optic degraded by high energy pulses of UV. It is also possible to use other optical attenuation methods of either polarized or unpolarized high energy pulses laser sources.

Although the laser apparatus 11 has been described principally in connection with an excimer laser angioplasty procedure, it should be appreciated that the laser apparatus can be utilized in other applications. For example, it can be used in non-ablative processing such as in photolithography. In photolithography it is not the energy per pulse as in laser angioplasty that is important, but rather the total ultraviolet laser energy which is absorbed in the photoresist to obtain a proper exposure. In such an application, the laser apparatus 11 of the present invention can be utilized to measure the accumulated dose by utilizing the internal monitor 64 to actively monitor the energy which has been transferred to the photoresist. Thus, the accumulated dose supplied to the photoresist could be monitored. As the accumulated desired dose is approached, the laser energy introduced into the photoresist can be reduced as the process nears the full dosage and stop the lasing as the accumulated dosage approaches a preset value to prevent overdosing. Other applications of the laser apparatus 11 can utilize similar principles within the scope of the present invention.

Alternatively, in such a non-ablative procedure the thin film polarizer 46 is rotated with a constant rotational velocity such that the polarized light transmission from the rotating polarizer element is a smoothly varying sine-wave. The triggering of the pulsed laser 12 is then timed to emit light during the time when the polarizer 46 is at the proper rotational angle with respect to the direction of polarization of the laser, effecting transmission of the desired amount of laser energy. For very high pulsed laser firing repetition rates, triggering the laser to fire at a given time is easier than mechanically moving an attenuator in the beam path. It is easy to maintain the rotational velocity of the attenuator constant, and/or to electro-optically measure the rotational position of the attenuator, and trigger the laser to fire when the proper transmission (angle of polarization mismatch) is available. This permits the delivery of very precise amounts of total laser energy or fluence for a process where the total delivered dose is critical. Such a process might take a few shots at the nominal maximum laser output energy, measure and sum the amount of energy or fluence actually delivered in those shots, and then begin delivering lower energy shots (more attenuated) until the target total dose is achieved with the desired precision.

What is claimed is:

1. In an apparatus using a pulsed laser source, an ultraviolet laser producing a plurality of laser pulses in a laser beam, an optical attenuator disposed in the laser beam to attenuate the individual pulse energy in the laser beam to provide an attenuated pulsed laser beam without substantial spatial distortion or angular deviation, pick-off means for sensing the energy in the attenuated laser beam and means coupled to the pick-off means for controlling the optical attenuator to vary the individual pulse energy in the attenuated laser beam to thereby vary the pulse output fluence from the apparatus, said optical attenuator being free of degradation after repeated pulses.

2. Apparatus as in claim 1 wherein said ultraviolet laser is an excimer laser having pulse energy fluences greater than $50/mJ/cm^2$ and output beam cross sectional area greater than $1 \times 1/cm^2$.

3. Apparatus as in claim 1 wherein said pick-off means includes a wedge disposed in the laser beam for deflecting a small fraction of the energy in the laser beam away from the laser beam and means for detecting the energy deflected from the laser beam.

4. Apparatus as in claim 1 for use with a fiber-optic based catheter having proximal and distal extremities wherein said apparatus further comprises a coupler for receiving the attenuated laser beam, said coupler having means adapted to connect the proximal extremity of the catheter to the coupler and a coupling lens disposed in the attenuated laser beam for focussing the beam into the coupler.

5. Apparatus as in claim 4 wherein said coupling lens forms a beam waist in the laser beam to provide a beam waist area in the vicinity of the coupler.

6. Apparatus as in claim 5 wherein said means for coupling the proximal extremity of the catheter into the coupler includes means for connecting the proximal extremity of the catheter into the Rayleigh range of the beam waist area.

7. Apparatus as in claim 6 wherein said fiber optic based catheter is provided with a fiber optic bundle having a cross sectional area in the proximal extremity and wherein said coupling lens provides a laser spot in the coupler which has a cross-sectional area in size which is greater than the cross-sectional area of the fiber optic bundle in the proximal extremity of the catheter.

8. Apparatus as in claim 7 wherein said laser beam in the coupler has a spot size which overfills the cross-sectional area of the fiber optic bundle at the proximal extremity of the catheter.

9. Apparatus as in claim 8 wherein the spot size in the coupler is determined by the equation $1-(A_1/A_2)$, where $A_1$ is the cross-sectional area of the fiber optic bundle and $A_2$ is the cross-sectional area of the laser beam spot.

10. Apparatus as in claim 1 wherein said means coupled to the pick-off means includes a controller with a single manual control thereon whereby the output fluence from the apparatus can be adjusted by operation of the manual control.

11. Apparatus as in claim 10 together with means for sensing the total output of the laser and for providing an electrical signal and connecting the electrical signal into the controller.

12. In an apparatus using a pulsed laser source, a laser producing a plurality of laser pulses in a laser beam, an optical attenuator disposed in the laser beam to attenuate the individual pulse energy in the laser beam to provide an attenuated pulsed laser beam without substantial spatial distortion or angular deviation, pick-off means for sensing the energy in the attenuated laser beam and means coupled to the pick-off means for controlling the optical attenuator to vary the individual pulse energy in the attenuated laser beam to thereby vary the pulse output fluence from the apparatus, said optical attenuator being an optically contacted thin film polarizer and being free of degradation after repeated pulses.

13. In an apparatus using a pulsed laser source, a laser producing a plurality of laser pulses in a laser beam, an optical attenuator disposed in the laser beam to attenuate the individual pulse energy in the laser beam to provide an attenuated pulsed laser beam without substantial spatial distortion or angular deviation, pick-off means for sensing the energy in the attenuated laser beam and means coupled to the pick-off means for controlling the optical attenuator to vary the individual pulse energy in the attenuated laser beam to thereby vary the pulse output fluence from the apparatus, said optical attenuator being free of degradation after repeated pulses, said laser beam having a predetermined polarization, said optical attenuator having a preferred axis of transmission, the preferred axis of transmission being aligned at an angle of rotation with respect to the direction of polarization of the laser beam, said means coupled to the pick-off means for controlling the optical attenuator to vary the output fluence including means for rotating the optical attenuator about its preferred axis of transmission.

14. In an apparatus using a pulsed laser source, the apparatus for use with a fiber-optic based catheter having proximal and distal extremities and being provided with a fiber optic bundle having a cross sectional area in the proximal extremity, a laser producing a plurality of laser pulses in a laser beam, an optical attenuator disposed in the laser beam to attenuate the individual pulse energy in the laser beam to provide an attenuated pulsed laser beam without substantial spatial distortion or angular deviation, pick-off means for sensing the energy in the attenuated laser beam and means coupled to the pick-off means for controlling the optical attenuator to vary the individual pulse energy in the attenuated laser beam to thereby vary the pulse output fluence from the apparatus, said optical attenuator being free of degradation after repeated pulses, a coupler for receiving the attenuated laser beam, said coupler having means adapted to connect the proximal extremity of the catheter to the coupler and a coupling lens disposed in the attenuated laser beam for focusing the beam into the coupler, said coupling lens forming a beam waist in the laser beam to provide a beam waist area in the vicinity of the coupler, said means for coupling the proximal extremity of the catheter into the coupler including means for connecting the proximal extremity of the catheter into the Rayleigh range of the beam waist area, said coupling lens providing a laser spot in the coupler which has a cross-sectional area in size which is greater than the cross-sectional area of the fiber optic bundle in the proximal extremity of the catheter, said laser beam in the coupler having a spot size which overfills the cross-sectional area of the fiber optic bundle at the proximal extremity of the catheter, the laser beam being rectangular in cross section and the fiber optic bundle being rectangular in cross section.

15. In a method for optically controlling the output energy of individual pulses of a ultraviolet high energy large aperture pulsed laser at an output coupler for use with a fiber optic catheter having proximal and distal extremities, optically attenuating the ultraviolet laser beam to vary the pulse energy in the individual pulses to provide a predetermined output fluence, and coupling the predetermined output fluence into the output coupler and then into the proximal extremity of the fiber optic catheter.

16. A method as in claim 15 together with the step of forming a waist in the laser beam in the vicinity of the coupler.

17. A method as in claim 16 together with the step of positioning the proximal extremity of the catheter in the vicinity of the waist within the Rayleigh number.

18. A method as in claim 17 together with the step of providing an optical beam spot in the coupler which is of a size to overfill the fiber optic bundle in the catheter.

19. A method as in claim 15 together with the step of diverting a small portion of the attenuated laser beam, sensing the diverted laser beam to ascertain the energy content, establishing a set point for the attenuated laser beam, and controlling the optical attenuation of the attenuated laser beam in response to the set point and the energy detected in the diverted laser beam.

20. A method as in claim 19 wherein the set point is established by comparing the energy fluence at the distal extremity of the catheter and the energy fluence at the proximal extremity of the catheter.

21. A method as in claim 20 together with the step of measuring the total laser energy from the laser to ascertain the energy content prior to attenuation of the laser beam and utilizing the information from the laser energy to control the attenuation of the attenuated laser beam.

22. A method as in claim 15 together with the step of monitoring the accumulated energy output from the coupler.

23. In an apparatus using a pulsed laser source, a laser producing a plurality of laser pulses in a laser beam, an optical attenuator disposed in the laser beam to attenuate the individual pulse energy in the laser beam to provide an attenuated pulsed laser beam without substantial spatial distortion or angular deviation, pick-off means for sensing the energy in the attenuated laser beam and means coupled to the pick-off means for controlling the optical attenuator to vary the individual pulse energy in the attenuated laser beam to thereby vary the pulse output fluence from the apparatus, said optical attenuator being free of degradation after repeated pulses, an optical coupler and a multifiber optic bundle angioplasty catheter having its proximal end disposed in the vicinity of the coupler, said optical attenuator varying the energy fluence into the optical coupler and into the proximal end of the multifiber optic bundle angioplasty catheter.

24. In an apparatus using a pulsed laser source, a laser producing a plurality of laser pulses in a laser beam, an optical attenuator disposed in the laser beam to attenuate the individual pulse energy in the laser beam to provide an attenuated pulsed laser beam without substantial spatial distortion or angular deviation, pick-off means for sensing the energy in the attenuated laser beam and means coupled to the pick-off means for controlling the optical attenuator to vary the individual pulse energy in the attenuated laser beam to thereby vary the pulse output fluence from the apparatus, said optical attenuator being free of degradation after repeated pulses, said laser being a pulsed excimer XeCl laser with output near 308 nm wavelength and having pulse duration of at least 100 nsec FWHM.

25. In an apparatus using a pulsed laser source, the apparatus for use with a fiber-optic based catheter having proximal and distal extremities, a laser producing a plurality of laser pulses in a laser beam, an optical attenuator disposed in the laser beam to attenuate the individual pulse energy in the laser beam to provide an attenuated pulsed laser beam without substantial spatial distortion or angular deviation, pick-off means for sensing the energy in the attenuated laser beam and means coupled to the pick-off means for controlling the optical attenuator to vary the individual pulse energy in the attenuated laser beam to thereby vary the pulse output fluence from the apparatus, said optical attenuator being free of degradation after repeated pulses, a coupler for receiving the attenuated laser beam, said coupler having means adapted to connect the proximal extremity of the catheter to the coupler and a coupling lens disposed in the attenuated laser beam for focusing the beam into the coupler, said coupling lens forming a beam waist in the laser beam to provide a beam waist area in the vicinity of the coupler, said means for coupling the proximal extremity of the catheter into the coupler including means for connecting the proximal extremity of the catheter into the Rayleigh range of the beam waist area, the beam waist area being of a size which can accommodate fiber optic catheters having different fiber optic bundle sizes.

\* \* \* \* \*